(12) United States Patent
Chen et al.

(10) Patent No.: US 11,753,626 B2
(45) Date of Patent: Sep. 12, 2023

(54) TUMOR CELL SUSPENSION CULTURES AND RELATED METHODS

(71) Applicant: Beijing Percans Oncology Co., Ltd., Beijing (CN)

(72) Inventors: Yiyou Chen, San Jose, CA (US); Zhen Yang, Beijing (CN); Yihong Zhang, Calabasas, CA (US)

(*) Notice: Subject to any disclaimer, the term of this patent is extended or adjusted under 35 U.S.C. 154(b) by 218 days.

(21) Appl. No.: 16/082,691

(22) PCT Filed: Mar. 9, 2017

(86) PCT No.: PCT/US2017/021683
§ 371 (c)(1),
(2) Date: Sep. 6, 2018

(87) PCT Pub. No.: WO2017/156341
PCT Pub. Date: Sep. 14, 2017

(65) Prior Publication Data
US 2019/0085297 A1    Mar. 21, 2019

(30) Foreign Application Priority Data

Mar. 9, 2016 (WO) ............... PCT/CN2016/075947

(51) Int. Cl.
| | |
|---|---|
| C12N 5/00 | (2006.01) |
| C12N 5/09 | (2010.01) |
| G01N 33/50 | (2006.01) |
| C12N 5/04 | (2006.01) |
| G01N 33/574 | (2006.01) |

(52) U.S. Cl.
CPC ......... *C12N 5/0693* (2013.01); *C12N 5/0062* (2013.01); *G01N 33/5011* (2013.01); *C12N 5/04* (2013.01); *C12N 2513/00* (2013.01); *G01N 33/574* (2013.01); *G01N 2510/00* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2008/0152624 A1 | 6/2008 | Paludan et al. | |
| 2009/0117655 A1 | 5/2009 | Kubota et al. | |
| 2013/0012404 A1 | 1/2013 | Inoue | |
| 2013/0071925 A1 | 3/2013 | Skribek et al. | |
| 2014/0154735 A1 | 6/2014 | Sundstrom et al. | |
| 2014/0243227 A1* | 8/2014 | Clevers ............... | C12N 5/0679 506/9 |
| 2014/0256037 A1 | 9/2014 | Sato et al. | |
| 2014/0328808 A1 | 11/2014 | Watanabe et al. | |
| 2016/0061817 A1* | 3/2016 | Xian ..................... | C12N 15/113 424/172.1 |
| 2019/0284536 A1 | 9/2019 | Zhang et al. | |

FOREIGN PATENT DOCUMENTS

| | | |
|---|---|---|
| CN | 102439135 A | 5/2012 |
| CN | 103237888 A | 8/2013 |
| CN | 104024401 A | 9/2014 |
| EP | 2 772 534 A1 | 9/2014 |
| EP | 2 878 664 B1 | 7/2018 |
| JP | 2013-208104 A | 10/2013 |
| JP | 2014-516562 A | 7/2014 |
| JP | 2014-526680 A | 10/2014 |
| JP | 2014-223087 A | 12/2014 |
| JP | 2014-532431 A | 12/2014 |
| JP | 2016-028569 A | 3/2016 |
| WO | WO-2008125846 A2 | 10/2008 |
| WO | WO 2010/009121 A2 | 1/2010 |
| WO | WO 2010/009121 A3 | 1/2010 |
| WO | WO 2012/065067 A2 | 5/2012 |
| WO | WO-2012093173 A1 | 7/2012 |
| WO | WO 2012/168930 A2 | 12/2012 |
| WO | WO 2013/037789 A1 | 3/2013 |
| WO | WO 2011/090068 A1 | 5/2013 |
| WO | WO 2013/061608 A1 | 5/2013 |
| WO | WO 2013/067498 A1 | 5/2013 |
| WO | WO 2014/072465 A1 | 5/2014 |
| WO | WO 2014/117021 A2 | 7/2014 |
| WO | WO 2014/152321 A1 | 9/2014 |
| WO | WO 2014/153294 A1 | 9/2014 |
| WO | WO 2014/172340 A1 | 10/2014 |
| WO | WO 2016/081554 A1 | 5/2016 |

OTHER PUBLICATIONS

StemPro® hESC SFM; pp. 1-3; downloaded Sep. 29, 2021.*
StemPro® hESC SFM data pp. 1-2; downloaded Sep. 29, 2021.*
Kondo et al., 2010; Supporting Information Kondo et al. 10.1073/pnas.1015938108 SI Materials and Methods pp. 1-10.*
Extended European Search Report dated Aug. 14, 2020 for European Application No. 17872054.6, 8 pages.
Boehnke, K. et al., "Assay Establishment and Validation of a High-Throughput Screen Platform for three-Dimensional Patient-Derived Colon Cancer Organoid Cultures," Journal of Biomolecular Screening, 21 (9):931-941 (2016).
Lippert, T. H. et al., "Current Status of Methods to Assess Cancer Drug Resistance," International Journal of Medical Sciences, 8(3):245-253 (2011).
International Search Report and Written Opinion dated Jun. 9, 2017 for International Application No. PCT/US2017/21683, 7 pages.
International Search Report and Written Opinion dated Aug. 23, 2017 for International Application No. PCT/CN2016/106619, 8 pages.
International Search Report and Written Opinion dated Nov. 29, 2017 for International Application No. PCT/CN2017/086556, 8 pages.

(Continued)

*Primary Examiner* — Maria G Leavitt
(74) *Attorney, Agent, or Firm* — COOLEY LLP

(57) ABSTRACT

Provided are suspension-based cell culture systems and media for the timely and efficient proliferation of human tumor cell clusters from a patient, and related methods of evaluating the potential responsiveness of the tumor cells and the patient to one or more therapeutic agents.

8 Claims, 4 Drawing Sheets

(56) References Cited

OTHER PUBLICATIONS

International Search Report and Written Opinion dated Mar. 29, 2018 for International Application No. PCT/US2017/62863, 11 pages.
Chico, L. K. et al., "Targeting protein kinases in central nervous system disorders," Nature Reviews Drug Discovery, 8:892-909 (2009).
Endo, H. et al., "Spheroid Culture of Primary Lung Cancer Cells with Neuregulin 1/HER3 Pathway Activation," Journal of Thoracic Oncology, 8(2):131-139 (2013).
Kondo, J. et al., "Retaining cell-cell contact enables preparation and culture of spheroids composed of pure primary cancer cells from colorectal cancer," PNAS, 108(15):6235-6240 (2011).
Liu, X. F. et al., "ROCK Inhibitor and Feeder Cells Induce the Conditional Reprogramming of Epithelial Cells," American Journal of Pathology, 180(2):599-607 (2012).
Maley, C. C. et al., "Genetic clonal diversity predicts progression to esophageal adenocarcinoma," Nature Genetics, 38(4):468-473 (2006).
Merlo, L. M. F. et al., "A Comprehensive Survey of Clonal Diversity Measures in Barrett's Esophagus as Biomarkers of Progression to Esophageal Adenocarcinoma," Cancer Prev Res, 3(11):1388-1397 (2010).
Sachs, N. & Clevers, H., "Organoid cultures for the analysis of cancer phenotypes," Current Opinion in Genetics & Development, 24:68-73 (2014).
Shibata, D., "Clonal diversity in tumor progression," Nature Genetics, 38(4):402-403 (2006).
Weiswald, L.-B. et al., "A short-term colorectal cancer sphere culture as a relevant tool for human cancer biology investigation," British Journal of Cancer, 108:1720-1731 (2013); doi: 10.1038/bjc.2013.132.
Extended European Search Report dated Jul. 29, 2019 for European Application No. 17764153.7, 12 pages.
Li, H.-z. et al., "Suspension culture combined with chemotherapeutic agents for sorting of breast cancer stem cells," BMC Cancer, 8:135 (2008), 7 pages; doi: 10.1 186/1471-2407-8-135.
Liu, Y. et al., "A novel chemical-defined medium with bFGF and N2B27 supplements supports undifferentiated growth in human embryonic stem cells," Biochemical and Biophysical Research Communications, 346:131-139 (2006).
Lu, J. et al., "Defined culture conditions of human embryonic stem cells," PNAS, 103(15):5688-5693 (2006).
Sato, T. et al., "Long-term Expansion of Epithelial Organoids From Human Colon, Adenoma, Adenocarcinoma, and Barrett's Epithelium," Gastroenterology, 141:1762-1772 (2011).
Communication pursuant to Article 94(3) dated Jun. 8, 2021 for European Application No. 17764153.7, 10 pages.
Toshiro, S. et al., "Supplementary Data: Long-term Expansion of Epithelial Organoids From Human Colon, Adenoma, Adenocarcinoma, and Barrett's Epithelium," Gastroenterology, 141(5):1762-1772 (2011).
Non-Final Office Action dated Jul. 21, 2022 for U.S. Appl. No. 16/348,705, 28 pages.

Bender, et al., "Activation of caspases measured in situ by binding of fluorochrome-labeled inhibotors of caspases (FLICA): correlation with DNA fragmentation," 259: 308-313 (Year: 2000).
Comley, J., "Progress made in applying 3D cell culture technologies," Drug Discovery World Winter 2013/2014 (Year: 2013), 18 pages; https://www.ddw-online.com/media/32/13d-cell-culture.pdf.
Gangavarapu, K.J., et al., "Isolation and application of prostate side population cells based on dye cycle violet efflux," Current Protocols in Toxicology, Chapter Unit 22.2, p. 1-18. (Year: 2011).
Kubben, F.J.G.B., et al., "Proliferating cell nuclear antigen (PCNA): a new marker to study human colonic cell proliferation," Gut 35: 530-535. (Year: 1994).
Llames, S., et al., "Feeder layer cell action and applications," Tissue Engineering, 21 (4): 345-353. (Year: 2015).
Maiese, K. & Chong, Z. Z., "Nicotinamide: necessary nutrient emerges as a novel cryoprotectant for the brain," Trends in Pharmacological Sciences, 24(4): 228-232 (Year: 2003).
Pierzchalska, M., et al., "Prostaglandin e2 supports growth of chicken embryo intestinal organoids in Matrigel matrix," Biotechniques, 52(5): 307-315. (Year: 2012).
Van Der Valk, J. et al., "Optimization of chemically defined cell culture media—Replacing fetal bovine serum in mammalian in vitro methods," Toxicology in Vitro, 24:1053-1063 (2010).
Yamane, I., et al., "Role of bovine albumin in a serum-free suspension cell culture medium (38823)," Proceedings of the Society for Experimental Biology and Medicine, 149: 439-442. (Year: 1975).
Kondo, J. et al., "Retaining cell-cell contact enables preparation and culture of spheroids composed of pure primary cancer cells from colorectal cancer," PNAS, 108(15):6235-6240 (2011), Supporting Information, 10 pages.
Jian et al., "The effect of Noggin protein on the proliferation of human osteosarcoma cell line MG63", Orthopedic Biomechanics Materials and Clinical Study (2009); vol. 6, No. 3, pp. 41-44, with English Abstract, 4 pages.
Yunfei et al., "Expression of BMP-2 in osteosarcoma of the jaw bone and its clinical significance", Journal of Practical Oncology (2004); vol. 9, No. 6, with English Abstract, 4 pages.
Final Office Action for U.S. Appl. No. 16/348,705 dated Apr. 12, 2023, 28 pages.
Kim et al., "Generation of orthotopic and heterotopic human pancreatic cancer xenografts in immunodeficient mice," Nature Protocols , 2009, vol. 4(11), pp. 1670-1680.
Libre Texts, Selective and Differential Media. Chapter 6.3C in Culturing Microorganisms. (Year: 2021), 2 pages; https://bio.libretexts.org/Bookshelves/Microbiology/Microbiology_(Boundless)/06%3A_Culturing_Microorganisms/6.03%3A_Culturing_Bacteria/6.3C%3A_Selective_and_Differential_Media.
First Office Action and Search Report dated Apr. 2, 2021 for Chinese Application No. 201780007304.2, with English translation, 14 pages.
Notice of Reasons for Rejection dated Nov. 4, 2020 for Japanese Application No. 2018-538846, with English language translation, 14 pages.
Ning, Z. et al., "Isolation and identification of tumor stem-like cells in bladder cancer cell line T2," Anatomical Research, 35(2):131-134 (2013). English Abstract.

\* cited by examiner

TUMOR CELL SUSPENSION CULTURES AND RELATED METHODS

CROSS-REFERENCE TO RELATED APPLICATION

This application is a § 371 national phase application of International Application No. PCT/US2017/201683, filed Mar. 9, 2017, which claims priority to PCT/CN2016/075947, filed Mar. 9, 2016, each of which is incorporated by reference in its entirety.

BACKGROUND

Technical Field

Embodiments of the present disclosure relate to suspension-based cell culture systems and media for the timely and efficient proliferation of human tumor cell clusters from a patient, and related methods of evaluating the potential responsiveness of the tumor cells and the patient to one or more therapeutic agents.

Description of the Related Art

Despite constant efforts to improve diagnostics and therapeutics, cancer remains a leading cause of death worldwide. The diversity or heterogeneity of cancer presents an obstacle to the development of new therapies and also makes it difficult to identify likely responders. Moreover, many cancer therapies are challenged by primary and acquired resistance, including additional point mutations and alternative pathways that bypass the targets of therapeutic reagents.

Future successful therapies will likely rely on a comprehensive analysis of events underlying the tumor progression and the metastatic processes, together with the development of relevant model systems that could be easily manipulated in order to accurately evaluate the efficacy of chemotherapeutic agents and combinations. As one example, primary cultures of cancer cells using matrix-embedded, three-dimensional (3D) cultures are increasingly used to investigate cancer biology and predict chemosensitivity for individual patients. However, the conditions for such matrix-embedded primary cultures of cancer cells are currently not optimized. Moreover, such primary cultures can be laborious, and include the potential for low cancer cell viability, contamination by host cells, and results that are difficult to reproduce, among other potential issues.

Thus, it is necessary to develop methods and compositions by which primary cancer cells can be cultured in 3D as feasibly and effectively as cell lines, and in a timely manner.

BRIEF DESCRIPTION OF THE DRAWINGS

FIG. 3A shows the proliferation markers for four different patient samples, and FIG. 3B shows the proliferation markers for one exemplary patient sample over the course of one week.

BRIEF SUMMARY

Figure 1A:
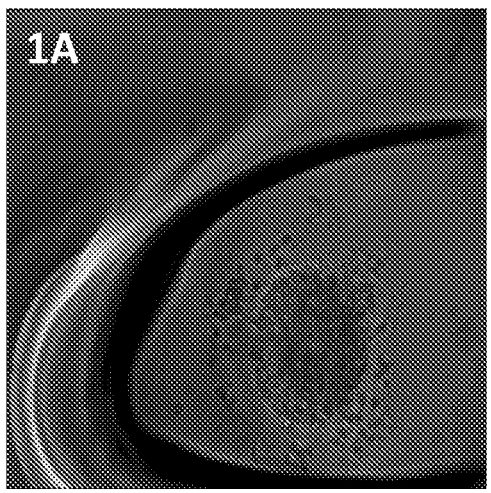
FIGS. 1A-1D show that tumor cells clusters were successfully isolated from colon/rectal tumors surgically remove from a patient, and cultured in suspension in a defined growth media.
Figure 1B:
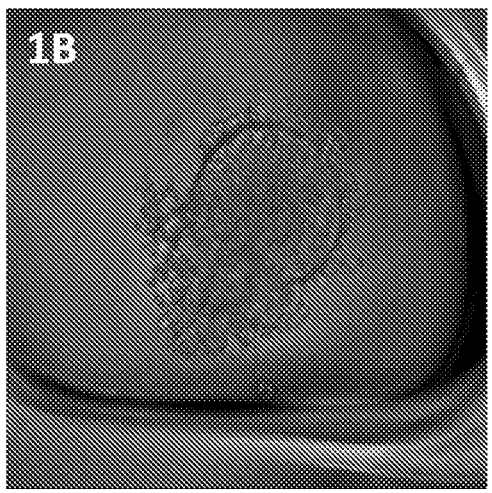
Figure 1C:
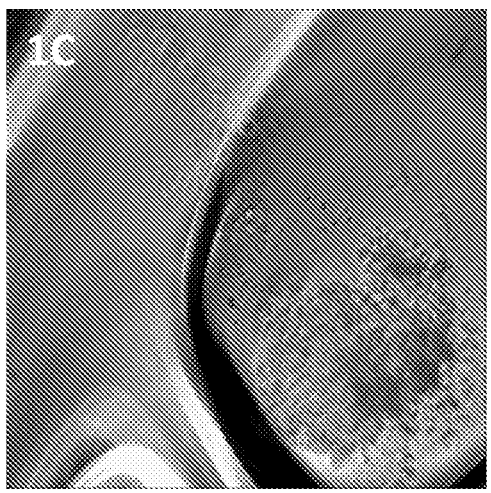
Figure 1D:
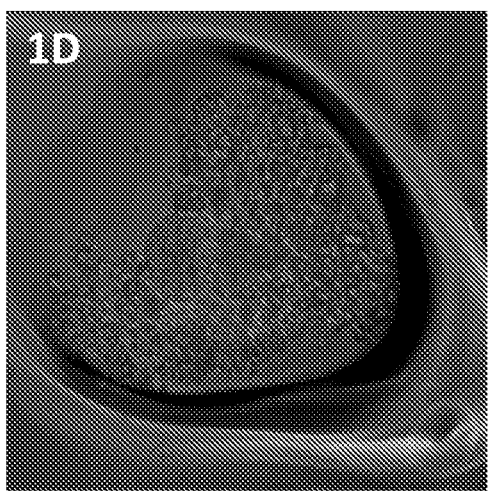

Embodiments of the present disclosure relate to a medium suspension (or media suspensions), comprising a population of human tumor cell clusters from a human patient, wherein the medium suspension provides at least about 10% proliferation of the tumor cell clusters within about 14 days.

In certain embodiments, the medium suspension provides at least about 10, 20, 30, 40, 50, 60, 70, 80, 90, or 100% proliferation of the human tumor cell clusters within about 14, 13, 12, 11, 10, 9, 8, 7, 6, or 5 days. In some embodiments, the medium suspension provides at least about 20-30% proliferation of the human tumor cell clusters within about 7 days. In certain embodiments, the medium suspension provides at least about 60% proliferation of the human tumor cell clusters within about 7 days.

In certain embodiments, the medium suspension comprises a defined medium. In some embodiments, the medium suspension is serum-free or substantially serum-free.

In certain embodiments, the medium suspension comprises or further comprises one or more components selected from DMEM/F-12, Wnt3A, basic fibroblast growth factor (bFGF), insulin, transferrin, bovine serum albumin (BSA), cholesterol, B-cell activating factor (BAFF), and 2-mercaptoethanol. In some embodiments, the medium suspension comprises 2, 3, 4, 5, 6, 7, 8, or 9 of the components selected from DMEM/F-12, Wnt3A, bFGF, insulin, transferrin, bovine serum albumin (BSA), cholesterol, B-cell activating factor (BAFF), and 2-mercaptoethanol. In particular embodiments, the medium suspension comprises DMEM/F-12, Wnt3A, bFGF, insulin, transferrin, bovine serum albumin (BSA), cholesterol, B-cell activating factor (BAFF), and 2-mercaptoethanol.

In certain embodiments, the medium suspension comprises or further comprises one or more components selected from nicotinamide, noggin, R-spondin-1, Y27632, fibroblast growth factor 10 (FGF10), and VO-OHpic. In some embodiments, the medium suspension comprises 2, 3, 4, 5, or 6 of the components selected from nicotinamide, noggin, R-spondin-1, Y27632, FGF10, and VO-OHpic. In specific embodiments, the medium suspension comprises nicotinamide, noggin, R-spondin-1, Y27632, FGF10, and VO-OHpic.

In certain embodiments, the medium suspension comprises or further comprises one or more components selected from epidermal growth factor (EGF), hepatocyte growth factor (HGF), insulin-like growth factor (IGF), vascular endothelial growth factor (VEGF), platelet-derived growth factor (PDGF), N2 Supplement, B27, prostaglandin E2 (PGE-2), and N-Acetyl-L-cysteine. In certain embodiments, the medium suspension comprises 2, 3, 4, 5, 6, 7, 8, or 9 of the components selected from EGF, HGF, IGF, VEGF, PDGF, N2, B27, PGE2, N-Acetyl-L-cysteine. In particular embodiments, the medium suspension comprises EGF, HGF, IGF, VEGF, PDGF, N2, B27, PGE2, and N-Acetyl-L-cysteine.

In certain embodiments, the medium suspension comprises or further comprises nicotinamide, noggin, R-spondin-1, Y27632, EGF, HGF, IGF, VEGF, PDGF, N2, B27, PGE2, N-Acetyl-L-cysteine, FGF10, and VO-OHpic.

In some embodiments, the medium suspension does not comprise an extracellular matrix component, for example, matrigel, collagen, laminin, or fibronectin.

In certain embodiments, the medium suspension comprises the human tumor cell clusters are lung cancer cells, colon cancer cells, gastric cancer cell, or breast cancer cells from a human patient. In some embodiments, the medium suspension comprises the human tumor cell clusters are isolated from an immunodeficient animal xenografted with human tumor cells and/or tissues from a human patient. In certain embodiments, the medium suspension comprises the human tumor cell clusters are isolated directly from a tumor sample removed from a human patient, optionally selected from surgical samples, biopsies, pleural effusion, and ascetic fluid.

Also included are methods of proliferating human tumor cells, comprising obtaining a population of human tumor cells from a sample, and culturing the population of human tumor cell clusters in a medium suspension as described herein. Some methods comprise culturing the human tumor cell clusters in the medium suspension for about 14 days or less. Some methods comprise culturing the human tumor cell clusters in the medium suspension for about 14, 13, 12, 11, 10, 9, 8, 7, 6, or 5 days or less. Particular methods comprise culturing the human tumor cell clusters in the medium suspension for about 7 days or less.

Also included are methods of testing responsiveness of a human patient to a therapeutic agent, comprising
obtaining or receiving a population of tumor cell clusters from the human patient;
culturing the population of tumor cell clusters in a medium suspension as defined in any one of the preceding claims;
administering the therapeutic agent to the medium suspension; and
measuring tumor cell proliferation and/or tumor cell apoptosis in the population of tumor cells,
wherein a decrease in tumor cell proliferation and/or an induction in tumor cell apoptosis is indicative of responsiveness of the human patient to the therapeutic agent, and wherein a lack of decrease in tumor cell proliferation and/or induction of tumor cell apoptosis is indicative of resistance of the human patient to the therapeutic agent.

Some methods comprise administering the therapeutic agent on the same day as culturing the population of tumor cell clusters in the medium suspension.

Certain methods comprise administering the therapeutic agent at least one day after culturing the population of tumor cell clusters in the medium suspension. Particular methods comprise administering the therapeutic agent about or within about 1, 2, 3, 4, 5, 6, or 7 days after culturing the population of tumor cell clusters in the medium suspension.

Some methods comprise measuring tumor cell proliferation and/or tumor cell apoptosis in the population of tumor cells within about 14 days of administering the therapeutic agent. Some methods comprise measuring tumor cell proliferation and/or tumor cell apoptosis in the population of tumor cells within about 14, 13, 12, 11, 10, 9, 8, 7, 6, or 5 days of administering the therapeutic agent. Specific methods comprise measuring tumor cell proliferation and/or tumor cell apoptosis in the population of tumor cells within about 7, 6, or 5 days of administering the therapeutic agent.

In some embodiments, the step of measuring tumor cell proliferation comprises measuring a cellular proliferation marker. In some embodiments, the cellular proliferation marker is selected from one or more of $^3$H-thymidine, bromodeoxyuridine (BrdU), 5-ethynyl-2'-deoxyuridine (Edu), Ki-67, and proliferating cell nuclear antigen (PCNA).

In certain embodiments, the step of measuring tumor cell apoptosis comprises measuring a cellular apoptosis marker. In some embodiments, the cellular apoptosis marker is selected from one or more of fluorochrome-labeled inhibitors of Caspases (FLICA), caspase activation, poly ADP ribose polymerase (PARP) cleavage, DRAQ5, DRAQ7, and terminal deoxynucleotidyl transferase (TdT) dUTP nick-end labeling (TUNEL) assay.

DETAILED DESCRIPTION

Embodiments of the present disclosure relate to the discovery of defined media and related suspension cell cultures that achieve the reliable and timely proliferation of primary human tumor cell clusters, whether derived directly from patients or from patient-derived xenografts (PDXs). The suspension cell cultures can be used, inter alia, to evaluate the potential responsiveness of patient tumors to one or more therapeutic agents, and provide the advantage of identifying optimal treatment options for the patient in a relatively short time frame, for example, in less than one or two weeks from the time of culture.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, certain preferred methods and materials are described herein. All publications and references, including but not limited to patents and patent applications, cited in this specification are incorporated by reference in their entireties as if each individual publication or reference were specifically and individually indicated to be incorporated by reference. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

By "isolated" is meant material that is substantially or essentially free from components that normally accompany it in its native state.

The term "modulating" includes "increasing" or "enhancing," as well as "decreasing" or "reducing," typically in a statistically significant or a physiologically significant amount as compared to a control. An "increased" or "enhanced" amount is typically a "statistically significant" amount, and may include an increase that is about or at least about 1.2, 1.4, 1.6, 1.8, 2, 3, 4, 5, 6, 7, 8, 9, 10, 15, 20, 30, 50, 60, 70, 80, 90, 100, 200, 300, 400, 500, 1000 times, or about or at least about 5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000%, the amount produced by no composition or a control composition, sample, or test subject (including all integers and ranges in between). A "decreased" or "reduced" amount is typically a "statistically significant" amount, and may include a decrease that is about or at least about 1.2, 1.4, 1.6, 1.8, 2, 3, 4, 5, 6, 7, 8, 9, 10, 15, 20, 30, 50, 60, 70, 80, 90, 100, 200, 300, 400, 500, 1000 times, or about or at least about 5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000%, the amount produced by no composition or a control composition, sample, or test subject (including all integers and ranges in between).

In certain embodiments, the "purity" of the tumor cell clusters in a medium or suspension culture may be specifically defined. For instance, certain media or suspension cultures may comprise tumor cell clusters that are about or at least about 50%, 55%, 60%, 65%, 70%, 75%, 80%, 85%, 90%, 95%, 100% pure, including all integers and ranges in between), relative to other cell types, for example, non-cancerous host cells or animal cells (e.g., for xenograft-derived tumor cell clusters).

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Substantially" or "essentially" means nearly totally or completely, for instance, 95% or greater of some given quantity.

As noted above, certain embodiments relate to a medium suspension, comprising a population of tumor cell clusters from a human patient, wherein the medium suspension provides at least about 10% proliferation of the tumor cell clusters within about 14 days. Thus, in these and related embodiments, the tumor cell clusters grow in suspension cultures, for example, as clumps in suspension, rather than as adherent cultures.

In some embodiments, the medium suspension provides about or at least about 10, 20, 30, 40, 50, 60, 70, 80, 90, or 100% proliferation of the tumor cell clusters within about 14, 13, 12, 11, 10, 9, 8, 7, 6, or 5 days (including all combinations, integers, and ranges in between).

For example, particular medium suspensions provide about or at least about 10-15, 10-20, 10-25, 10-30, 10-35, 10-40, 10-45, 10-50, 10-55, 10-60, 10-65, 10-70, 10-75, 10-80, 10-85, 10-90, 10-95, or 10-100% proliferation of the tumor cell clusters, or about or at least about 15-20, 15-25, 15-30, 15-35, 15-40, 15-45, 15-50, 15-55, 15-60, 15-65, 15-70, 15-75, 15-80, 15-85, 15-90, 15-95, or 15-100% proliferation of the tumor cell clusters, or about or at least about 20-25, 20-30, 20-35, 20-40, 20-45, 20-50, 20-55, 20-60, 20-65, 20-70, 20-75, 20-80, 20-85, 20-90, 20-95, or 20-100% proliferation of the tumor cell clusters, or about or at least about 25-30, 25-35, 25-40, 25-45, 25-50, 25-55, 25-60, 25-65, 25-70, 25-75, 25-80, 25-85, 25-90, 25-95, or 25-100% proliferation of the tumor cell clusters, or about or at least about 30-35, 30-40, 30-45, 30-50, 30-55, 30-60, 30-65, 30-70, 30-75, 30-80, 30-85, 30-90, 30-95, or 30-100% proliferation of the tumor cell clusters, or about or at least about 35-40, 35-45, 35-50, 35-55, 35-60, 35-65, 35-70, 35-75, 35-80, 35-85, 35-90, 35-95, or 35-100% proliferation of the tumor cell clusters, or about or at least about 40-45, 40-50, 40-55, 40-60, 40-65, 40-70, 40-75, 40-80, 40-85, 40-90, 40-95, or 40-100% proliferation of the tumor cell clusters, or about or at least about 45-50, 45-55, 45-60, 45-65, 45-70, 45-75, 45-80, 45-85, 45-90, 45-95, or 45-100% proliferation of the tumor cell clusters, or about or at least about 50-55, 50-60, 50-65, 50-70, 50-75, 50-80, 50-85, 50-90, 50-95, or 50-100% proliferation of the tumor cell clusters, or about or at least about 55-60, 55-65, 55-70, 55-75, 55-80, 55-85, 55-90, 55-95, or 55-100% proliferation of the tumor cell clusters, or about or at least about 60-65, 60-70, 60-75, 60-80, 60-85, 60-90, 60-95, or 60-100% proliferation of the tumor cell clusters, or about or at least about 65-70, 65-75, 65-80, 65-85, 65-90, 65-95, or 65-100% proliferation of the tumor cell clusters, or about or at least about 70-80, 70-85, 70-90, 70-95, or 70-100% proliferation of the tumor cell clusters, or about or at least about 75-80, 75-85, 75-90, 75-95, or 75-100% proliferation of the tumor cell clusters, or about or at least about 80-85, 80-90, 80-95, or 80-100% proliferation of the tumor cell clusters, or about or at least about 85-90, 85-95, or 85-100% proliferation of the tumor cell clusters, or about or at least about 90-95, or 90-100% proliferation of the tumor cell clusters, or about or at least about 95-100% proliferation of the tumor cell clusters, optionally within about 14, 13, 12, 11, 10, 9, 8, 7, 6, or 5 days, or within about 5-14, 6-14, 7-14, 8-14, 9-14, 10-14, 11-14, 12-14, or 13-14 days, or within about 5-13, 6-13, 7-13, 8-13, 9-13, 10-13, 11-13, or 12-13 days, or within about 5-12, 6-12, 7-12, 8-12, 9-12, 10-12, or 11-12 days, or within about 5-11, 6-11, 7-11, 8-11, 9-11, or 10-11 days, or within about 5-10, 6-10, 7-10, 8-10, or 9-10 days, or within about 5-9, 6-9, 7-9, or 8-9 days, or within about 5-8, 6-8, or 7-8 days, or within about 5-7 or 6-7 days, or within about 5-6 days, including all combinations thereof. Specific embodiments provide at least about 20-30% proliferation of the tumor cell clusters within about 7 days, or at least about 60% proliferation of the tumor cell clusters within about 7 days.

In some embodiments, the medium suspension of tumor cell clusters comprises a "defined medium." In certain embodiments, a "defined medium" is a growth medium suitable for the in vitro or ex vivo cell culture of human or animal cells in which all of the chemical components are known. In some embodiments, a defined medium is "serum-free" or "substantially serum-free," that is, the medium lacks or substantially lacks added serum, for example, fetal bovine serum (FBS) or fetal calf serum (FCS).

In some embodiments, the defined medium comprises a basal media such as DMEM, F12, RPMI 1640, or a combination thereof, for example, DMEM/F12, which is supplemented with additional components, for example, growth factors, antioxidants, and/or energy sources. Thus, in particular embodiments, the defined medium comprises Dulbecco's Modified Eagles Medium (DMEM), Ham's Nutrient Mixture (F12), RPMI 1640, or DMEM/F12. In some embodiments, the medium comprises DMEM/F12, for example, at a ratio of about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10.

In certain embodiments, the defined medium comprises one or more components, for example, 1, 2, 3, 4, 5, 6, 7, or 8 components, which are selected from Wnt3A, basic fibroblast growth factor (bFGF), insulin, transferrin, bovine serum albumin (BSA), cholesterol, B-cell activating factor (BAFF), and 2-mercaptoethanol, including all combinations of the foregoing. Particular embodiments comprise DMEM/F-12 in combination with one or more components, for example, 1, 2, 3, 4, 5, 6, 7, or 8 components, which are selected from Wnt3A, bFGF, insulin, transferrin, bovine serum albumin (BSA), cholesterol, B-cell activating factor (BAFF), and 2-mercaptoethanol. Specific embodiments comprise DMEM/F-12, Wnt3A, bFGF, insulin, transferrin, bovine serum albumin (BSA), cholesterol, B-cell activating factor (BAFF), and 2-mercaptoethanol.

In certain embodiments, the concentration of Wnt3A ranges from about 0.1-10,000 or 1-1000 ng/ml, or from about 0.1-1000, 1-1000, 10-1000, 20-1000, 30-1000, 40-1000, 50-1000, 60-1000, 70-1000, 80-1000, 90-1000, 100-1000, 200-1000, 300-1000, 400-1000, 500-1000, 600-1000, 700-1000, 800-1000, 900-1000 ng/ml, or from about 0.1-500, 1-500, 10-500, 20-500, 30-500, 40-500, 50-500, 60-500, 70-500, 80-500, 90-500, 100-500, 200-500, 300-500, 400-500 ng/ml, or from about 0.1-400, 1-400, 10-400, 20-400, 30-400, 50-400, 40-400, 60-400, 70-400, 80-400, 90-400, 100-400, 200-400, 300-400 ng/ml, or from about 0.1-300, 1-300, 10-300, 20-300, 30-300, 40-300, 50-300, 60-300, 70-300, 80-300, 90-300, 100-300, 200-300 ng/ml, or from about 0.1-200, 1-200, 10-200, 20-200, 30-200, 40-200, 50-200, 60-200, 70-200, 80-200, 90-200, 100-200 ng/ml, or from about 0.1-150, 1-150, 10-150, 20-150, 30-150, 40-150, 50-150, 60-150, 70-150, 80-150, 90-150, 100-150 ng/ml, or from about 0.1-120, 1-120, 10-120, 20-120, 30-120, 40-120, 50-120, 60-120, 70-120, 80-120, 90-120, 100-120 ng/ml, or from about 0.1-100, 1-100, 10-100, 20-100, 30-100, 40-100, 50-100, 60-100, 70-100, 80-100, 90-100 ng/ml. In specific embodiments, the Wnt3A is a human or mouse Wnt3A protein, for example, a recombinant human or mouse Wnt3A protein.

In certain embodiments, the concentration of bFGF ranges from about 0.1-100 or 1-10 ng/ml, or from about 0.1-100, 0.2-100, 0.3-100, 0.4-100, 0.5-100, 0.6-100, 0.7-100, 0.8-100, 0.9-100, 1-100, 2-100, 3-100, 4-100, 5-100, 10-100, 50-100 ng/ml, or from about 0.1-50, 0.2-50, 0.3-50, 0.4-50, 0.5-50, 0.6-50, 0.7-50, 0.8-50, 0.9-50, 1-50, 2-50, 3-50, 4-50, 5-50, 10-50 ng/ml, or from about 0.1-10, 0.2-10, 0.3-10, 0.4-10, 0.5-10, 0.6-10, 0.7-10, 0.8-10, 0.9-10, 1-10, 2-10, 3-10, 4-10, 5-10 ng/ml, or from about 0.1-5, 0.2-5, 0.3-5, 0.4-5, 0.5-5, 0.6-5, 0.7-5, 0.8-5, 0.9-5, 1-5, 2-5, 3-5, 4-5 ng/ml. In specific embodiments, the bFGF is a human or mouse bFGF protein, for example, a recombinant human or mouse bFGF protein.

In certain embodiments, the concentration of insulin ranges from about 0.1-10,000 or 1-1000 or 100-500 µg/ml, or from about 0.1-1000, 1-1000, 10-1000, 20-1000, 30-1000, 40-1000, 50-1000, 60-1000, 70-1000, 80-1000, 90-1000, 100-1000, 200-1000, 300-1000, 400-1000, 500-1000, 600-1000, 700-1000, 800-1000, 900-1000 µg/ml, or from about 0.1-500, 1-500, 10-500, 20-500, 30-500, 40-500, 50-500, 60-500, 70-500, 80-500, 90-500, 100-500, 200-500, 300-500, 400-500 µg/ml, or from about 0.1-400, 1-400, 10-400, 20-400, 30-400, 50-400, 40-400, 60-400, 70-400, 80-400, 90-400, 100-400, 200-400, 300-400 µg/ml, or from about 0.1-300, 1-300, 10-300, 20-300, 30-300, 40-300, 50-300, 60-300, 70-300, 80-300, 90-300, 100-300, 200-300 µg/ml, or from about 0.1-200, 1-200, 10-200, 20-200, 30-200, 40-200, 50-200, 60-200, 70-200, 80-200, 90-200, 100-200 µg/ml. In specific embodiments, the insulin is a human or mouse insulin protein, for example, a recombinant human or mouse insulin protein. In some embodiments, the insulin is an solution or powder from pancreatic extracts, for example, bovine pancreas-derived powder or solution.

In certain embodiments, the concentration of transferrin ranges from about 0.1-10,000 or 1-1000 or 1-100 µg/ml, or from about 0.1-1000, 1-1000, 10-1000, 20-1000, 30-1000, 40-1000, 50-1000, 60-1000, 70-1000, 80-1000, 90-1000, 100-1000, 200-1000, 300-1000, 400-1000, 500-1000, 600-1000, 700-1000, 800-1000, 900-1000 µg/ml, or from about 0.1-500, 1-500, 10-500, 20-500, 30-500, 40-500, 50-500, 60-500, 70-500, 80-500, 90-500, 100-500, 200-500, 300-500, 400-500 µg/ml, or from about 0.1-400, 1-400, 10-400, 20-400, 30-400, 50-400, 40-400, 60-400, 70-400, 80-400, 90-400, 100-400, 200-400, 300-400 µg/ml, or from about 0.1-300, 1-300, 10-300, 20-300, 30-300, 40-300, 50-300, 60-300, 70-300, 80-300, 90-300, 100-300, 200-300 µg/ml, or from about 0.1-200, 1-200, 10-200, 20-200, 30-200, 40-200, 50-200, 60-200, 70-200, 80-200, 90-200, 100-200 µg/ml, or from about 0.1-150, 1-150, 10-150, 20-150, 30-150, 40-150, 50-150, 60-150, 70-150, 80-150, 90-150, 100-150 µg/ml, or from about 0.1-120, 1-120, 10-120, 20-120, 30-120, 40-120, 50-120, 60-120, 70-120, 80-120, 90-120, 100-120 µg/ml, or from about 0.1-100, 1-100, 10-100, 20-100, 30-100, 40-100, 50-100, 60-100, 70-100, 80-100, 90-100 µg/ml.

In certain embodiments, the concentration of BSA is about 5, 10, 15, 20, 25, 30, 35, 40, 45, 50%, or ranges from about 1-50%, or from about 5-50, 10-50, 15-50, 20-50, 25-50, 30-50, 35-50, 40-50, 45-50%, or from about 5-45, 10-45, 15-45, 20-45, 25-45, 30-45, 35-45, 40-45%, or from about 5-40, 10-40, 15-40, 20-40, 25-40, 30-40, 35-40%, or from about 5-35, 10-35, 15-35, 20-35, 25-35, 30-35%, or from about 5-30, 10-30, 15-30, 20-30, 25-30%, or from about 5-25, 10-25, 15-25, 20-25%, or from about 5-20, 10-20, 15-20%, or from about 5-15, 10-15%, or from about 5-10%.

In certain embodiments, the concentration of cholesterol is about or ranges from about at about 0.1, 0.5, 1, 1.5, 2, 2.5, 3, 3.5, 4, 4.5, 5, 5.5, 6, 6.5, 7, 7.5, 8, 8.5, 9, 9.5, or 10×, or ranges from about 0.01-10× or 0.1-10×, or from about 0.1-10, 0.2-10, 0.3-10, 0.4-10, 0.5-10, 0.6-10, 0.7-10, 0.8-10, 0.9-10, 1-10, 2-10, 5-10×, or from about 0.1-5, 0.2-5, 0.3-5, 0.4-5, 0.5-5, 0.6-5, 0.7-5, 0.8-5, 0.9-5, 1-5, 2-5×, or from about 0.1-4, 0.2-4, 0.3-4, 0.4-4, 0.5-4, 0.6-4, 0.7-4, 0.8-4, 0.9-4, 1-4, 2-4×, or from about 0.1-3, 0.2-3, 0.3-3, 0.4-3, 0.5-3, 0.6-3, 0.7-3, 0.8-3, 0.9-3, 1-3, 2-3×, or from about 0.1-2, 0.2-2, 0.3-2, 0.4-2, 0.5-2, 0.6-2, 0.7-2, 0.8-2, 0.9-2, 1-2×, optionally relative to a 50× or 100× or 250× stock. Cholesterol (250×) is commercially available, for example, from ThermoFisher Scientific.

In certain embodiments, the concentration of BAFF ranges from about 0.1-10,000 or 1-1000 ng/ml, or from about 0.1-1000, 1-1000, 10-1000, 20-1000, 30-1000, 40-1000, 50-1000, 60-1000, 70-1000, 80-1000, 90-1000, 100-1000, 200-1000, 300-1000, 400-1000, 500-1000, 600-1000, 700-1000, 800-1000, 900-1000 ng/ml, or from about 0.1-500, 1-500, 10-500, 20-500, 30-500, 40-500, 50-500, 60-500, 70-500, 80-500, 90-500, 100-500, 200-500, 300-500, 400-500 ng/ml, or from about 0.1-400, 1-400, 10-400, 20-400, 30-400, 50-400, 40-400, 60-400, 70-400, 80-400, 90-400, 100-400, 200-400, 300-400 ng/ml, or from about 0.1-300, 1-300, 10-300, 20-300, 30-300, 40-300, 50-300, 60-300, 70-300, 80-300, 90-300, 100-300, 200-300 ng/ml, or from about 0.1-200, 1-200, 10-200, 20-200, 30-200, 40-200, 50-200, 60-200, 70-200, 80-200, 90-200, 100-200 ng/ml, or from about 0.1-150, 1-150, 10-150, 20-150, 30-150, 40-150, 50-150, 60-150, 70-150, 80-150, 90-150, 100-150 ng/ml, or from about 0.1-120, 1-120, 10-120, 20-120, 30-120, 40-120, 50-120, 60-120, 70-120, 80-120, 90-120, 100-120 ng/ml, or from about 0.1-100, 1-100, 10-100, 20-100, 30-100, 40-100, 50-100, 60-100, 70-100, 80-100, 90-100 ng/ml. In specific embodiments, the BAFF is a human or mouse BAFF protein, for example, a recombinant human or mouse BAFF protein.

In certain embodiments, the concentration of 2-mercaptoethanol ranges from about 0.01-100 or 0.1-1 mM, or from about 0.01-10, 0.02-10, 0.03-10, 0.04-10, 0.05-10, 0.06-10, 0.07-10, 0.08-10, 0.09-10, 0.1-10, 0.5-10, 1-10, or 5-10 mM, or from about 0.01-5, 0.02-5, 0.03-5, 0.04-5, 0.05-5, 0.06-5, 0.07-5, 0.08-5, 0.09-5, 0.1-5, 0.5-5, 1-5 mM, or from about 0.01-2, 0.02-2, 0.03-2, 0.04-2, 0.05-2, 0.06-2, 0.07-2, 0.08-2, 0.09-2, 0.1-2, 0.5-2, 1-2 mM, or from about 0.01-1, 0.02-1, 0.03-1, 0.04-1, 0.05-1, 0.06-1, 0.07-1, 0.08-1, 0.09-1, 0.1-1, 0.5-1 mM, or from about 0.01-0.5, 0.02-0.5, 0.03-0.5, 0.04-0.5, 0.05-0.5, 0.06-0.5, 0.07-0.5, 0.08-0.5, 0.09-0.5, or 0.1-0.5 mM, or from about 0.01-0.4, 0.02-0.4, 0.03-0.4, 0.04-0.4, 0.05-0.4, 0.06-0.4, 0.07-0.4, 0.08-0.4, 0.09-0.4, or 0.1-0.4 mM, or from about 0.01-0.3, 0.02-0.3, 0.03-0.3, 0.04-0.3, 0.05-0.3, 0.06-0.3, 0.07-0.3, 0.08-0.3, 0.09-0.3, or 0.1-0.3 mM, or from about 0.01-0.2, 0.02-0.2, 0.03-0.2, 0.04-0.2, 0.05-0.2, 0.06-0.2, 0.07-0.2, 0.08-0.2, 0.09-0.2, or 0.1-0.2 mM.

In certain embodiments, and further to the components above, the suspension medium comprises one or more components, for example, 1, 2, 3, 4, 5, or 6 components, which are selected from nicotinamide, noggin, R-spondin-1, Y27632, fibroblast growth factor 10 (FGF10), and VO-OHpic, including all combinations of the foregoing. In some embodiments, the suspension medium comprises nicotinamide, noggin, R-spondin-1, Y27632, FGF10, and VO-OHpic.

In certain embodiments, the concentration of nicotinamide ranges from about 0.1-1000, 0.5-1000, 1-1000, 5-1000, 10-1000, 50-1000, 100-1000, 500-1000 mM, or from about 0.1-500, 0.5-500, 1-500, 5-500, 10-500, 50-500, 100-500 mM, or from about 0.1-100, 0.5-100, 1-100, 5-100, 10-100, 50-100 mM, or from about 0.1-50, 0.5-50, 1-50, 5-50, 10-50 mM, or from about 0.1-40, 0.5-40, 1-40, 5-40, 10-40 mM, or from about 0.1-30, 0.5-30, 1-30, 5-30, 10-30 mM, or from about 0.1-20, 0.5-20, 1-20, 5-20, 10-20 mM, or from about 0.1-10, 0.5-10, 1-10, 5-10 mM, or from about 0.1-5, 0.5-5, 1-5 mM, or from about 0.1-1 or 0.5-1 mM.

In certain embodiments, the concentration of noggin ranges from about 0.1-10,000 or 1-1000 ng/ml, or from about 0.1-1000, 1-1000, 10-1000, 20-1000, 30-1000, 40-1000, 50-1000, 60-1000, 70-1000, 80-1000, 90-1000, 100-1000, 200-1000, 300-1000, 400-1000, 500-1000, 600-1000, 700-1000, 800-1000, 900-1000 ng/ml, or from about 0.1-500, 1-500, 10-500, 20-500, 30-500, 40-500, 50-500, 60-500, 70-500, 80-500, 90-500, 100-500, 200-500, 300-500, 400-500 ng/ml, or from about 0.1-400, 1-400, 10-400, 20-400, 30-400, 50-400, 40-400, 60-400, 70-400, 80-400, 90-400, 100-400, 200-400, 300-400 ng/ml, or from about 0.1-300, 1-300, 10-300, 20-300, 30-300, 40-300, 50-300, 60-300, 70-300, 80-300, 90-300, 100-300, 200-300 ng/ml, or from about 0.1-200, 1-200, 10-200, 20-200, 30-200, 40-200, 50-200, 60-200, 70-200, 80-200, 90-200, 100-200 ng/ml, or from about 0.1-150, 1-150, 10-150, 20-150, 30-150, 40-150, 50-150, 60-150, 70-150, 80-150, 90-150, 100-150 ng/ml, or from about 0.1-120, 1-120, 10-120, 20-120, 30-120, 40-120, 50-120, 60-120, 70-120, 80-120, 90-120, 100-120 ng/ml, or from about 0.1-100, 1-100, 10-100, 20-100, 30-100, 40-100, 50-100, 60-100, 70-100, 80-100, 90-100 ng/ml. In specific embodiments, the noggin is a human or mouse noggin protein, for example, a recombinant human or mouse noggin protein.

In certain embodiments, the concentration of R-spondin-1 ranges from about 0.1-10,000 or 1-1000 or 100-1000 ng/ml, or from about 0.1-10,000, 1-10,000, 10-10,000, 20-10,000, 30-10,000, 40-10,000, 50-10,000, 60-10,000, 70-10,000, 80-10,000, 90-10,000, 100-10,000, 200-10,000, 300-10,000, 400-10,000, 500-10,000, 1000-10,000, 5000-10,000 ng/ml, or from about 0.1-5000, 1-5000, 10-5000, 20-5000, 30-10,000, 40-5000, 50-5000, 60-5000, 70-5000, 80-5000, 90-5000, 100-5000, 200-5000, 300-5000, 400-5000, 500-5000, 1000-5000 ng/ml, or from about 0.1-1000, 1-1000, 10-1000, 20-1000, 30-1000, 40-1000, 50-1000, 60-1000, 70-1000, 80-1000, 90-1000, 100-1000, 200-1000, 300-1000, 400-1000, 500-1000, 600-1000, 700-1000, 800-1000, 900-1000 ng/ml, or from about 0.1-800, 1-800, 10-800, 20-800, 30-800, 40-800, 50-800, 60-800, 70-800, 80-800, 90-800, 100-800, 200-800, 300-800, 400-800, 500-800, 600-800, 700-800 ng/ml, or from about 0.1-700, 1-700, 10-700, 20-700, 30-700, 40-700, 50-700, 60-700, 70-700, 80-700, 90-700, 100-700, 200-700, 300-700, 400-700, 500-700, 600-700 ng/ml, or from about 0.1-600, 1-600, 10-600, 20-600, 30-600, 40-600, 50-600, 60-600, 70-600, 80-600, 90-600, 100-600, 200-600, 300-600, 400-600, 500-600 ng/ml, or from about 0.1-500, 1-500, 10-500, 20-500, 30-500, 40-500, 50-500, 60-500, 70-500, 80-500, 90-500, 100-500, 200-500, 300-500, 400-500 ng/ml. In specific embodiments, the R-spondin-1 is a human or mouse R-spondin-1 protein, for example, a recombinant human or mouse R-spondin-1 protein.

In certain embodiments, the concentration of Y27632 ranges from about 0.1-1000, 0.5-1000, 1-1000, 5-1000, 10-1000, 50-1000, 100-1000, 500-1000 µM, or from about 0.1-500, 0.5-500, 1-500, 5-500, 10-500, 50-500, 100-500 µM, or from about 0.1-100, 0.5-100, 1-100, 5-100, 10-100, 50-100 µM, or from about 0.1-50, 0.5-50, 1-50, 5-50, 10-50 µM, or from about 0.1-40, 0.5-40, 1-40, 5-40, 10-40 µM, or from about 0.1-30, 0.5-30, 1-30, 5-30, 10-30 µM, or from about 0.1-20, 0.5-20, 1-20, 5-20, 10-20 µM, or from about 0.1-10, 0.5-10, 1-10, 5-10 µM, or from about 0.1-5, 0.5-5, 1-5 µM, or from about 0.1-1 or 0.5-1 µM.

In certain embodiments, the concentration of FGF10 ranges from about 0.1-10,000 or 1-1000 ng/ml, or from about 0.1-1000, 1-1000, 10-1000, 20-1000, 30-1000, 40-1000, 50-1000, 60-1000, 70-1000, 80-1000, 90-1000, 100-1000, 200-1000, 300-1000, 400-1000, 500-1000, 600-1000, 700-1000, 800-1000, 900-1000 ng/ml, or from about 0.1-500, 1-500, 10-500, 20-500, 30-500, 40-500, 50-500, 60-500, 70-500, 80-500, 90-500, 100-500, 200-500, 300-500, 400-500 ng/ml, or from about 0.1-400, 1-400, 10-400, 20-400, 30-400, 50-400, 40-400, 60-400, 70-400, 80-400, 90-400, 100-400, 200-400, 300-400 ng/ml, or from about 0.1-300, 1-300, 10-300, 20-300, 30-300, 40-300, 50-300, 60-300, 70-300, 80-300, 90-300, 100-300, 200-300 ng/ml, or from about 0.1-200, 1-200, 10-200, 20-200, 30-200, 40-200, 50-200, 60-200, 70-200, 80-200, 90-200, 100-200 ng/ml, or from about 0.1-150, 1-150, 10-150, 20-150, 30-150, 40-150, 50-150, 60-150, 70-150, 80-150, 90-150, 100-150 ng/ml, or from about 0.1-120, 1-120, 10-120, 20-120, 30-120, 40-120, 50-120, 60-120, 70-120, 80-120, 90-120, 100-120 ng/ml, or from about 0.1-100, 1-100, 10-100, 20-100, 30-100, 40-100, 50-100, 60-100, 70-100, 80-100, 90-100 ng/ml. In specific embodiments, the FGF10 is a human or mouse FGF10 protein, for example, a recombinant human or mouse FGF10 protein.

In certain embodiments, the concentration of VO-OHpic ranges from about 0.01-100, or 0.05-10, or 0.1-10 µM, or from about 0.01-10, 0.02-10, 0.03-10, 0.04-10, 0.05-10, 0.06-10, 0.07-10, 0.08-10, 0.09-10, 0.1-10, 0.5-10, 1-10, or 5-10 µM, or from about 0.01-5, 0.02-5, 0.03-5, 0.04-5, 0.05-5, 0.06-5, 0.07-5, 0.08-5, 0.09-5, 0.1-5, 0.5-5, 1-5 µM, or from about 0.01-2, 0.02-2, 0.03-2, 0.04-2, 0.05-2, 0.06-2, 0.07-2, 0.08-2, 0.09-2, 0.1-2, 0.5-2, 1-2 µM, or from about 0.01-1, 0.02-1, 0.03-1, 0.04-1, 0.05-1, 0.06-1, 0.07-1, 0.08-1, 0.09-1, 0.1-1, 0.5-1 µM, or from about 0.01-0.5, 0.02-0.5, 0.03-0.5, 0.04-0.5, 0.05-0.5, 0.06-0.5, 0.07-0.5, 0.08-0.5, 0.09-0.5, or 0.1-0.5 µM, or from about 0.01-0.4, 0.02-0.4, 0.03-0.4, 0.04-0.4, 0.05-0.4, 0.06-0.4, 0.07-0.4, 0.08-0.4, 0.09-0.4, or 0.1-0.4 µM, or from about 0.01-0.3, 0.02-0.3, 0.03-0.3, 0.04-0.3, 0.05-0.3, 0.06-0.3, 0.07-0.3, 0.08-0.3, 0.09-0.3, or 0.1-0.3 µM, or from about 0.01-0.2, 0.02-0.2, 0.03-0.2, 0.04-0.2, 0.05-0.2, 0.06-0.2, 0.07-0.2, 0.08-0.2, 0.09-0.2, or 0.1-0.2 µM. Particular examples of commercially available VO-OHpic include VO-OHpic trihydrate.

In certain embodiments, and further to the components above, the suspension medium comprises one or more components, for example, 1, 2, 3, 4, 5, 6, 7, 8, or 9 components, which are selected from epidermal growth factor (EGF), hepatocyte growth factor (HGF), insulin-like growth factor (IGF), vascular endothelial growth factor (VEGF), platelet-derived growth factor (PDGF), N2 Supplement, B27, prostaglandin E2 (PGE-2), and N-Acetyl-L-cysteine, including all combinations of the foregoing. In particular embodiments, and further to the components above, the suspension medium comprises EGF, HGF, IGF, VEGF, PDGF, N2, B27, PGE2, N-Acetyl-L-cysteine.

In certain embodiments, the concentration of EGF ranges from about 0.1-1000 or 1-100 ng/ml, or from about 0.1-1000, 0.5-1000, 1-1000, 5-1000, 10-1000, 50-1000, 100-1000, 500-1000 ng/ml, or from about 0.1-500, 0.5-500, 1-500, 5-500, 10-500, 50-500, 100-500 ng/ml, or from about 0.1-100, 0.5-100, 1-100, 5-100, 10-100, 50-100 ng/ml, or from about 0.1-50, 0.5-50, 1-50, 5-50, 10-50 ng/ml, or from about 0.1-40, 0.5-40, 1-40, 5-40, 10-40 ng/ml, or from about 0.1-30, 0.5-30, 1-30, 5-30, 10-30 ng/ml, or from about 0.1-20, 0.5-20, 1-20, 5-20, 10-20 ng/ml, or from about 0.1-10, 0.5-10, 1-10, 5-10 ng/ml, or from about 0.1-5, 0.5-5, 1-5 ng/ml, or from about 0.1-1 or 0.5-1 ng/ml. In specific embodiments, the EGF is a human or mouse EGF protein, for example, a recombinant human or mouse EGF protein.

In certain embodiments, the concentration of HGF ranges from about 0.1-1000 or 1-100 ng/ml, or from about 0.1-1000, 0.5-1000, 1-1000, 5-1000, 10-1000, 50-1000, 100-1000, 500-1000 ng/ml, or from about 0.1-500, 0.5-500, 1-500, 5-500, 10-500, 50-500, 100-500 ng/ml, or from about 0.1-100, 0.5-100, 1-100, 5-100, 10-100, 50-100 ng/ml, or from about 0.1-50, 0.5-50, 1-50, 5-50, 10-50 ng/ml, or from about 0.1-40, 0.5-40, 1-40, 5-40, 10-40 ng/ml, or from about 0.1-30, 0.5-30, 1-30, 5-30, 10-30 ng/ml, or from about 0.1-20, 0.5-20, 1-20, 5-20, 10-20 ng/ml, or from about 0.1-10, 0.5-10, 1-10, 5-10 ng/ml, or from about 0.1-5, 0.5-5, 1-5 ng/ml, or from about 0.1-1 or 0.5-1 ng/ml. In specific embodiments, the HGF is a human or mouse HGF protein, for example, a recombinant human or mouse HGF protein.

In certain embodiments, the concentration of IGF ranges from about 0.1-1000 or 1-100 ng/ml, or from about 0.1-1000, 0.5-1000, 1-1000, 5-1000, 10-1000, 50-1000, 100-1000, 500-1000 ng/ml, or from about 0.1-500, 0.5-500, 1-500, 5-500, 10-500, 50-500, 100-500 ng/ml, or from about 0.1-100, 0.5-100, 1-100, 5-100, 10-100, 50-100 ng/ml, or from about 0.1-50, 0.5-50, 1-50, 5-50, 10-50 ng/ml, or from about 0.1-40, 0.5-40, 1-40, 5-40, 10-40 ng/ml, or from about 0.1-30, 0.5-30, 1-30, 5-30, 10-30 ng/ml, or from about 0.1-20, 0.5-20, 1-20, 5-20, 10-20 ng/ml, or from about 0.1-10, 0.5-10, 1-10, 5-10 ng/ml, or from about 0.1-5, 0.5-5, 1-5 ng/ml, or from about 0.1-1 or 0.5-1 ng/ml. In specific embodiments, the IGF is a human or mouse IGF protein, for example, a recombinant human or mouse IGF protein.

In certain embodiments, the concentration of VEGF ranges from about 0.1-1000 or 1-100 ng/ml, or from about 0.1-1000, 0.5-1000, 1-1000, 5-1000, 10-1000, 50-1000, 100-1000, 500-1000 ng/ml, or from about 0.1-500, 0.5-500, 1-500, 5-500, 10-500, 50-500, 100-500 ng/ml, or from about 0.1-100, 0.5-100, 1-100, 5-100, 10-100, 50-100 ng/ml, or from about 0.1-50, 0.5-50, 1-50, 5-50, 10-50 ng/ml, or from about 0.1-40, 0.5-40, 1-40, 5-40, 10-40 ng/ml, or from about 0.1-30, 0.5-30, 1-30, 5-30, 10-30 ng/ml, or from about 0.1-20, 0.5-20, 1-20, 5-20, 10-20 ng/ml, or from about 0.1-10, 0.5-10, 1-10, 5-10 ng/ml, or from about 0.1-5, 0.5-5, 1-5 ng/ml, or from about 0.1-1 or 0.5-1 ng/ml. In specific embodiments, the VEGF is a human or mouse VEGF protein, for example, a recombinant human or mouse VEGF protein.

In certain embodiments, the concentration of PDGF ranges from about 0.1-1000 or 1-100 ng/ml, or from about 0.1-1000, 0.5-1000, 1-1000, 5-1000, 10-1000, 50-1000, 100-1000, 500-1000 ng/ml, or from about 0.1-500, 0.5-500, 1-500, 5-500, 10-500, 50-500, 100-500 ng/ml, or from about 0.1-100, 0.5-100, 1-100, 5-100, 10-100, 50-100 ng/ml, or from about 0.1-50, 0.5-50, 1-50, 5-50, 10-50 ng/ml, or from about 0.1-40, 0.5-40, 1-40, 5-40, 10-40 ng/ml, or from about 0.1-30, 0.5-30, 1-30, 5-30, 10-30 ng/ml, or from about 0.1-20, 0.5-20, 1-20, 5-20, 10-20 ng/ml, or from about 0.1-10, 0.5-10, 1-10, 5-10 ng/ml, or from about 0.1-5, 0.5-5, 1-5 ng/ml, or from about 0.1-1 or 0.5-1 ng/ml. In specific embodiments, the PDGF is a human or mouse PDGF protein, for example, a recombinant human or mouse PDGF protein.

In certain embodiments, the concentration of N2 is at about 0.1, 0.5, 1, 1.5, 2, 2.5, 3, 3.5, 4, 4.5, 5, 5.5, 6, 6.5, 7, 7.5, 8, 8.5, 9, 9.5, or 10×, or ranges from about 0.01-10× or 0.1-10×, or from about 0.1-10, 0.2-10, 0.3-10, 0.4-10, 0.5-10, 0.6-10, 0.7-10, 0.8-10, 0.9-10, 1-10, 2-10, 5-10×, or from about 0.1-5, 0.2-5, 0.3-5, 0.4-5, 0.5-5, 0.6-5, 0.7-5, 0.8-5, 0.9-5, 1-5, 2-5×, or from about 0.1-4, 0.2-4, 0.3-4, 0.4-4, 0.5-4, 0.6-4, 0.7-4, 0.8-4, 0.9-4, 1-4, 2-4×, or from about 0.1-3, 0.2-3, 0.3-3, 0.4-3, 0.5-3, 0.6-3, 0.7-3, 0.8-3, 0.9-3, 1-3, 2-3×, or from about 0.1-2, 0.2-2, 0.3-2, 0.4-2, 0.5-2, 0.6-2, 0.7-2, 0.8-2, 0.9-2, 1-2×, optionally relative to a 50× or 100× stock. N2 Supplement (100×) is commercially available, for example, from ThermoFisher Scientific and Stemcell Technologies.

In certain embodiments, the concentration of B27 is about 0.1, 0.5, 1, 1.5, 2, 2.5, 3, 3.5, 4, 4.5, 5, 5.5, 6, 6.5, 7, 7.5, 8, 8.5, 9, 9.5, or 10×, or ranges from about 0.01-10× or 0.1-10×, or from about 0.1-10, 0.2-10, 0.3-10, 0.4-10, 0.5-10, 0.6-10, 0.7-10, 0.8-10, 0.9-10, 1-10, 2-10, 5-10×, or from about 0.1-5, 0.2-5, 0.3-5, 0.4-5, 0.5-5, 0.6-5, 0.7-5, 0.8-5, 0.9-5, 1-5, 2-5×, or from about 0.1-4, 0.2-4, 0.3-4, 0.4-4, 0.5-4, 0.6-4, 0.7-4, 0.8-4, 0.9-4, 1-4, 2-4×, or from about 0.1-3, 0.2-3, 0.3-3, 0.4-3, 0.5-3, 0.6-3, 0.7-3, 0.8-3, 0.9-3, 1-3, 2-3×, or from about 0.1-2, 0.2-2, 0.3-2, 0.4-2, 0.5-2, 0.6-2, 0.7-2, 0.8-2, 0.9-2, 1-2×, optionally relative to a 50× or 100× stock. B27® Supplement (50×) is commercially available, for example, from ThermoFisher Scientific.

In certain embodiments, the concentration of PGE-2 is about or ranges from about 0.1-1000, 0.5-1000, 1-1000, 5-1000, 10-1000, 50-1000, 100-1000, 500-1000 nM, or from about 0.1-500, 0.5-500, 1-500, 5-500, 10-500, 50-500, 100-500 nM, or from about 0.1-100, 0.5-100, 1-100, 5-100, 10-100, 50-100 nM, or from about 0.1-50, 0.5-50, 1-50, 5-50, 10-50 nM, or from about 0.1-40, 0.5-40, 1-40, 5-40, 10-40 nM, or from about 0.1-30, 0.5-30, 1-30, 5-30, 10-30 nM, or from about 0.1-20, 0.5-20, 1-20, 5-20, 10-20 nM, or from about 0.1-10, 0.5-10, 1-10, 5-10 nM, or from about 0.1-5, 0.5-5, 1-5 nM, or from about 0.1-1 or 0.5-1 nM.

In certain embodiments, the concentration of N-Acetyl-L-cysteine ranges from about 0.1-100 or 0.1-10 or 0.5-10 mM, or from about 0.1-100, 0.2-100, 0.3-100, 0.4-100, 0.5-100, 0.6-100, 0.7-100, 0.8-100, 0.9-100, 1-100, 2-100, 3-100, 4-100, 5-100, 10-100, 50-100 mM, or from about 0.1-50, 0.2-50, 0.3-50, 0.4-50, 0.5-50, 0.6-50, 0.7-50, 0.8-50, 0.9-50, 1-50, 2-50, 3-50, 4-50, 5-50, 10-50 mM, or from about 0.1-10, 0.2-10, 0.3-10, 0.4-10, 0.5-10, 0.6-10, 0.7-10, 0.8-10, 0.9-10, 1-10, 2-10, 3-10, 4-10, 5-10 mM, or from about 0.1-5, 0.2-5, 0.3-5, 0.4-5, 0.5-5, 0.6-5, 0.7-5, 0.8-5, 0.9-5, 1-5, 2-5, 3-5, 4-5 mM, or from about 0.1-2, 0.2-2, 0.3-2, 0.4-2, 0.5-2, 0.6-2, 0.7-2, 0.8-2, 0.9-2, 1-2 mM.

In specific embodiments, the suspension medium comprises nicotinamide, noggin, R-spondin-1, Y27632, EGF, HGF, IGF, VEGF, PDGF, N2, B27, PGE2, N-Acetyl-L-cysteine, FGF10, and VO-OHpic.

In certain embodiments, the medium suspension excludes or otherwise does not comprise an extracellular matrix (ECM) component. Merely by way of illustration, the medium suspension does not comprise collagen, matrigel, laminin, and/or fibronectin.

In some embodiments, the tumor cell clusters are from obtained a human patient, for example, primary tumor cells derived directly from a human patient. In certain embodiments, the tumor cell clusters are isolated from an immunodeficient animal xenografted with tumor cells, that is, the tumor cells are patient-derived xenografts (PDXs). Particular examples of tumor cell clusters isolated directly from a patient or indirectly via PDXs include lung cancer cells, colon cancer cells, gastric cancer cell, and breast cancer cells. In some embodiments, the tumor cell clusters are isolated directly from a tumor sample removed from a human patient, examples of which include surgical samples, biopsies, pleural effusions, and ascites fluids. The tumor cells can be obtained directed from the patient, or from a physician or other healthcare provider, for example, which plays a role in the patient's healthcare and cancer treatment.

Also included are methods of proliferating human tumor cells, comprising obtaining a population of human tumor cell clusters from a sample (e.g., as described herein), and culturing the population of human tumor cell clusters in a medium suspension, as described herein. In some embodiments, the human tumor cell clusters are cultured in the medium suspension for about 14 days or less, or for about 14, 13, 12, 11, 10, 9, 8, 7, 6, or 5 days or less, or for about 5-14, 6-14, 7-14, 8-14, 9-14, 10-14, 11-14, 12-14, or 13-14 days or less, or for about 5-13, 6-13, 7-13, 8-13, 9-13, 10-13, 11-13, or 12-13 days or less, or for about 5-12, 6-12, 7-12, 8-12, 9-12, 10-12, or 11-12 days or less, or for about 5-11, 6-11, 7-11, 8-11, 9-11, or 10-11 days or less, or about 5-10, 6-10, 7-10, 8-10, or 9-10 days or less, or for about 5-9, 6-9, 7-9, or 8-9 days or less, or for about 5-8, 6-8, or 7-8 days or less, or for about 5-7 or 6-7 days or less.

In some embodiments, the methods provide for about or at least about 10, 20, 30, 40, 50, 60, 70, 80, 90, or 100% proliferation of the tumor cell clusters within about 14, 13, 12, 11, 10, 9, 8, 7, 6, or 5 days (including all combinations, integers, and ranges in between). For example, certain methods provide for about or at least about 10-15, 10-20, 10-25, 10-30, 10-35, 10-40, 10-45, 10-50, 10-55, 10-60, 10-65, 10-70, 10-75, 10-80, 10-85, 10-90, 10-95, or 10-100% proliferation of the tumor cell clusters, or for about or at least about 15-20, 15-25, 15-30, 15-35, 15-40, 15-45, 15-50, 15-55, 15-60, 15-65, 15-70, 15-75, 15-80, 15-85, 15-90, 15-95, or 15-100% proliferation of the tumor cell clusters, or for about or at least about 20-25, 20-30, 20-35, 20-40, 20-45, 20-50, 20-55, 20-60, 20-65, 20-70, 20-75, 20-80, 20-85, 20-90, 20-95, or 20-100% proliferation of the tumor cell clusters, or for about or at least about 25-30, 25-35, 25-40, 25-45, 25-50, 25-55, 25-60, 25-65, 25-70, 25-75, 25-80, 25-85, 25-90, 25-95, or 25-100% proliferation of the tumor cell clusters, or for about or at least about 30-35, 30-40, 30-45, 30-50, 30-55, 30-60, 30-65, 30-70, 30-75, 30-80, 30-85, 30-90, 30-95, or 30-100% proliferation of the tumor cell clusters, or for about or at least about 35-40, 35-45, 35-50, 35-55, 35-60, 35-65, 35-70, 35-75, 35-80, 35-85, 35-90, 35-95, or 35-100% proliferation of the tumor cell clusters, or for about or at least about 40-45, 40-50, 40-55, 40-60, 40-65, 40-70, 40-75, 40-80, 40-85, 40-90, 40-95, or 40-100% proliferation of the tumor cell clusters, or for about or at least about 45-50, 45-55, 45-60, 45-65, 45-70, 45-75, 45-80, 45-85, 45-90, 45-95, or 45-100% proliferation of the tumor cell clusters, or for about or at least about 50-55, 50-60, 50-65, 50-70, 50-75, 50-80, 50-85, 50-90, 50-95, or 50-100% proliferation of the tumor cell clusters, or for about or at least about 55-60, 55-65, 55-70, 55-75, 55-80, 55-85, 55-90, 55-95, or 55-100% proliferation of the tumor cell clusters, or for about or at least about 60-65, 60-70, 60-75, 60-80, 60-85, 60-90, 60-95, or 60-100% proliferation of the tumor cell clusters, or for about or at least about 65-70, 65-75, 65-80, 65-85, 65-90, 65-95, or 65-100% proliferation of the tumor cell clusters, or for about or at least about 70-80, 70-85, 70-90, 70-95, or 70-100% proliferation of the tumor cell clusters, or for about or at least about 75-80, 75-85, 75-90, 75-95, or 75-100% proliferation of the tumor cell clusters, or for about or at least about 80-85, 80-90, 80-95, or 80-100% proliferation of the tumor cell clusters, or for about or at least about 85-90, 85-95, or 85-100% proliferation of the tumor cell clusters, or for about or at least about 90-95, or 90-100% proliferation of the tumor cell clusters, or for about or at least about 95-100% proliferation of the tumor cell clusters, optionally within about 14, 13, 12, 11, 10, 9, 8, 7, 6, or 5 days, or within about 5-14, 6-14, 7-14, 8-14, 9-14, 10-14, 11-14, 12-14, or 13-14 days, or within about 5-13, 6-13, 7-13, 8-13, 9-13, 10-13, 11-13, or 12-13 days, or within about 5-12, 6-12, 7-12, 8-12, 9-12, 10-12, or 11-12 days, or within about 5-11, 6-11, 7-11, 8-11, 9-11, or 10-11 days, or within about 5-10, 6-10, 7-10, 8-10, or 9-10 days, or within about 5-9, 6-9, 7-9, or 8-9 days, or within about 5-8, 6-8, or 7-8 days, or within about 5-7 or 6-7 days, or within about 5-6 days of culture, including all combinations thereof. Specific methods provide for at least about 20-30% proliferation of the tumor cell clusters within about 7 days, or for at least about 60% proliferation of the tumor cell clusters within about 7 days.

As noted above, the suspension media and methods described herein can be used, inter alia, to evaluate the potential responsiveness of patient tumors to one or more therapeutic agents, and provide the advantage of identifying optimal treatment options for the patient in a relatively short time frame, for example, in less than one or two weeks. Thus, certain embodiments include methods of testing responsiveness of a human patient to a therapeutic agent (e.g., a drug or candidate drug), comprising obtaining a population of tumor cell clusters from the human patient; culturing the population of tumor cell clusters in a medium suspension as defined in any one of the preceding claims; administering a therapeutic agent or drug to the medium suspension; and measuring tumor cell proliferation and/or tumor cell apoptosis in the population of tumor cells.

In some embodiments, a decrease (e.g., statistically significant decrease) in tumor cell proliferation is indicative of responsiveness of the human patient (i.e., the tumor in the human patient) to the therapeutic agent, and in some embodiments, a lack of decrease (e.g., a lack of a statistically significant decrease) in tumor cell proliferation is indicative of resistance and likely non-responsiveness of the human patient (i.e., the tumor in the human patient) to the therapeutic agent. In some embodiments, an induction (e.g., statistically significant increase) in tumor cell apoptosis is indicative of responsiveness of the human patient (i.e., the tumor in the human patient) to the therapeutic agent. In particular embodiments, a lack of increase (e.g., a lack of a statistically significant increase) in tumor cell proliferation is indicative of resistance and likely non-responsiveness of the human patient (i.e., the tumor in the human patient) to the therapeutic agent. In certain embodiments, a decrease in tumor cell proliferation and an induction in tumor cell apoptosis is indicative of responsiveness of the human patient to the therapeutic agent, and a lack of decrease in tumor cell proliferation is indicative of resistance or likely non-responsiveness of the human patient to the therapeutic agent.

In some embodiments, the methods of testing responsiveness include administering the therapeutic agent on the same day (e.g., at the same time or substantially the same time) as culturing the population of tumor cell clusters in the medium suspension. Certain embodiment include administering the therapeutic agent within about 1, 2, 3, 4, 5, 6, 7, 8, 9, 10, 11, 12, 13, 14, 15, 16, 17, 18, 19, 20, 21, 22, 23, or 24 hours of culturing the population of tumor cell clusters in the medium suspension. Also included are methods of administering the therapeutic agent about or within about 1, 2, 3, 4, 5, 6, or 7 days after culturing the population of tumor cell clusters in the medium suspension, including methods of administering the therapeutic agent about or within about 1-7, 1-6, 1-5, 1-4, 1-3, 1-2, or 2-7, 2-6, 2-5, 2-4, 2-3, or 3-7, 3-6, 3-5, 3-4, or 4-7, 4-6, 4-5, or 5-7, 5-6, or 6-7 days after culturing the population of tumor cell clusters in the medium suspension.

Certain embodiments include the step of measuring tumor cell proliferation and/or tumor cell apoptosis in the population of tumor cells within about 14 days of administering the therapeutic agent, for example, within about 14, 13, 12, 11, 10, 9, 8, 7, 6, or 5 days of administering the therapeutic agent. Specific embodiments include the step of measuring tumor cell proliferation and/or tumor cell apoptosis in the population of tumor cells within about 5-14, 6-14, 7-14, 8-14, 9-14, 10-14, 11-14, 12-14, or 13-14 days, or within about 5-13, 6-13, 7-13, 8-13, 9-13, 10-13, 11-13, or 12-13 days, or within about 5-12, 6-12, 7-12, 8-12, 9-12, 10-12, or 11-12 days, or within about 5-11, 6-11, 7-11, 8-11, 9-11, or 10-11 days, or within about 5-10, 6-10, 7-10, 8-10, or 9-10 days, or within about 5-9, 6-9, 7-9, or 8-9 days, or within about 5-8, 6-8, or 7-8 days, or within about 5-7 or 6-7 days, or within about 5-6 days of administering the therapeutic agent.

In certain embodiments, the therapeutic agent or drug for testing is a small molecule. Exemplary small molecules include cytotoxic, chemotherapeutic, and anti-angiogenic agents, for instance, those that have been considered useful in the treatment of various cancers. Particular classes of small molecules include, without limitation, alkylating agents, anti-metabolites, anthracyclines, anti-tumor antibiotics, platinums, type I topoisomerase inhibitors, type II topoisomerase inhibitors, vinca alkaloids, and taxanes.

Specific examples of small molecules include chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, and paclitaxel, and pharmaceutically acceptable salts, acids or derivatives of any of the above. Additional examples of small molecules include imatinib, crizotinib, dasatinib, sorafenib, pazopanib, sunitinib, vatalanib, geftinib, erlotinib, AEE-788, dichoroacetate, tamoxifen, fasudil, SB-681323, and semaxanib (SU5416) (see Chico et al., Nat Rev Drug Discov. 8:829-909, 2009).

Further examples of small molecules include alkylating agents such as thiotepa, cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and docetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above.

Also included are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the therapeutic agent is an antibody or an antigen-binding fragment thereof. In certain embodiments, the antibody or antigen-binding fragment thereof or other polypeptide specifically binds to a cancer-associated antigen, or cancer antigen, for example, a cancer antigen expressed by the tumor cell clusters being tested. Exemplary cancer antigens include cell surface proteins such as cell surface receptors. Also included as cancer-associated antigens are ligands that bind to such cell surface proteins or receptors. In specific embodiments, the antibody or antigen-binding fragment specifically binds to a intracellular cancer antigen. In some embodiments, the cancer that associates with the cancer antigen is one or more of breast cancer, metastatic brain cancer, prostate cancer, gastrointestinal cancer, lung cancer, ovarian cancer, testicular cancer, head and neck cancer, stomach cancer, bladder cancer, pancreatic cancer, liver cancer, kidney cancer, squamous cell carcinoma, CNS or brain cancer, melanoma, non-melanoma cancer, thyroid cancer, endometrial cancer, epithelial tumor, bone cancer, or a hematopoietic cancer.

In particular embodiments, the antibody or antigen-binding fragment or other polypeptide specifically binds to at least one cancer-associated antigen, or cancer antigen, such as human Her2/neu, Her1/EGF receptor (EGFR), Her3, A33 antigen, B7H3, CD5, CD19, CD20, CD22, CD23 (IgE Receptor), C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), integrin $\alpha_v\beta_3$, integrin $\alpha_5\beta_1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and/or mesothelin.

In certain embodiments, the antibody is a therapeutic antibody, such as an anti-cancer therapeutic antibody, including antibodies such as 3F8, 8H9, abagovomab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, cetuximab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, trastuzumab, tucotuzumab (celmoleukin), ublituximab, urelumab, veltuzumab, volociximab, votumumab, and zalutumumab. Also included are fragments, variants, and derivatives of these antibodies.

Certain embodiments include testing the responsiveness to combinations of two or more therapeutic agents. Thus, certain methods include administering two or more therapeutic agents to the medium suspension, including combinations of any two or more of the foregoing, exemplary therapeutic agents.

Any variety of methods known in the art can be used to measure tumor cell proliferation and/or tumor cell apoptosis. For example, certain methods of measuring tumor cell proliferation include measuring one or more cellular proliferation markers. Exemplary cellular proliferation markers include $^3$H-thymidine, bromodeoxyuridine (BrdU), 5-ethynyl-2'-deoxyuridine (Edu), Ki-67, and proliferating cell nuclear antigen (PCNA). Thus, in certain embodiments, the step of measuring tumor cell proliferation comprises measuring a cellular proliferation marker, which is optionally selected from one or more of $^3$H-thymidine, BrdU, Edu, Ki-67, and PCNA, including combinations thereof.

Likewise, any variety of methods known in the art can be used to measure tumor cell apoptosis. "Apoptosis" refers generally to a process of programmed cell death that occurs in multicellular organisms, including biochemical events that lead to characteristic cell changes (e.g., morphology)

and cell death. Exemplary changes include blebbing, cell shrinkage, nuclear fragmentation, chromatin condensation, chromosomal DNA fragmentation, and global mRNA decay. Certain methods of measuring tumor cell apoptosis include measuring a cellular apoptosis marker. Exemplary cellular apoptosis markers include fluorochrome-labeled inhibitors of Caspases (FLICA), caspase activation, poly ADP ribose polymerase (PARP) cleavage, DRAQ5, DRAQ7, and a terminal deoxynucleotidyl transferase (TdT) dUTP nick-end labeling (TUNEL) assay. Thus, in certain embodiments, the step of measuring tumor cell apoptosis comprises measuring a cellular apoptosis marker, which is optionally selected from one or more of FLICA, PARP, DRAQ5, DRAQ7, and a TUNEL assay, including combinations thereof.

In certain aspects, these responsiveness tests or methods are performed at a diagnostic laboratory, and the results are then provided to the patient, or to a physician or other healthcare provider that plays a role in the patient's healthcare and cancer treatment. Particular embodiments thus include methods for providing the results of the tumor cell cluster responsiveness test to the patient, or to the physician or other healthcare provider. These results or data can be in the form of a hard-copy or paper-copy, or an electronic form, such as a computer-readable medium.

EXAMPLES

Example 1

Isolation and Analysis of Tumor Cell Clusters

Surgical specimen from colorectal cancer patients were obtained from Beijing Tumor Hospital after receiving patient consensus. Patient-derived xenograft tumor specimens were obtained from Nod/SCID mice inoculated with surgical tumor specimen from patients.

Briefly, the non-tumor tissues and the necrotic fractions were carefully removed from the tumor specimen. The tumor tissues were cut into small pieces less than 1 mm in diameter using scissors. Minced tumor fractions were transferred into a sterile 100-ml triangle glass flask loaded with a magnet stir bar. A 10-15 ml digestion media containing 0.25 U/ml Liberase DH was added into the minced tumor tissues to start enzyme digestion. The enzyme mixture was incubated at 37° C. for 1-2 hours with moderate stirring. The partially digested tumor cell clusters were filtered through a 100-µm cell retainer. The filtrates were re-filtered through a 40-µm cell restrainer. The tumor cell clusters retained on the 40-µm cell restrainer was collected, wash twice with HBSS, then re-suspended in a defined growth media supplemented with cell growth factors and small molecule inhibitors.

For ex vivo drug sensitivity assays, the tumor cell clusters were recovered in a defined growth medium overnight. The defined growth medium was StemPro hESC SFM supplement with Nicotinamide, Wnt3A, Noggin, R-spondin-1, and Y27632. The tumor cell clusters were then exposed to drug (e.g., Docetaxel at 2 µM (Cmax)) for 24 hours before the drug was washed away. Following exposure with drug, the tumor cell clusters were labeled with 5-ethynyl-2'-deoxyuridine (Edu) to assess the tumor cell proliferation rates. The labeling started at 48 hours after the drug exposure and continued for 96 hours. In the control group, tumor cell clusters received no drug exposure with media change, but were similarly labeled with Edu. The labeled tumor cell clusters were dissociated into single cells and fixed. The fixed cells were stained with Hoechst 33342 in PBS containing 0.2% Triton X-100 overnight at 4° C. The incorporated Edu was detected by Click-iT reaction where fixed cells were incubated with a reaction mixture containing 1× Click-iT Edu reaction buffer, $CuSO_4$, and azide-conjugated Alexa Fluor dye in the dark. The stained cells were washed with PBS before being distributed into a black wall plate for image acquisition and analysis.

For image acquisition and analysis, the stained tumor cells were imaged by a high-content screening (HCS) platform (Thermo Scientific Cellomics ArrayScan XTi HCS reader). The 10× objective was used to collect images. Twenty-five fields were imaged for each well, and more than 3000 cells were captured for the analysis. From the images two fluorescent signals were obtained from the HCS reader. Blue fluorescent signals recorded nucleus signals stained with Hoechst 33342, and green fluorescent signal detected the Edu incorporated in newly synthesized DNA. The Edu positive subpopulation cells percentage was calculated as percent of the total cell counts. The cut-off point for drug resistance in this ex vivo assay was defined as less than 90% inhibition of Edu incorporation when tumor cell clusters were exposed to 2 µM docetaxel for 24 hours.

Figure 2:
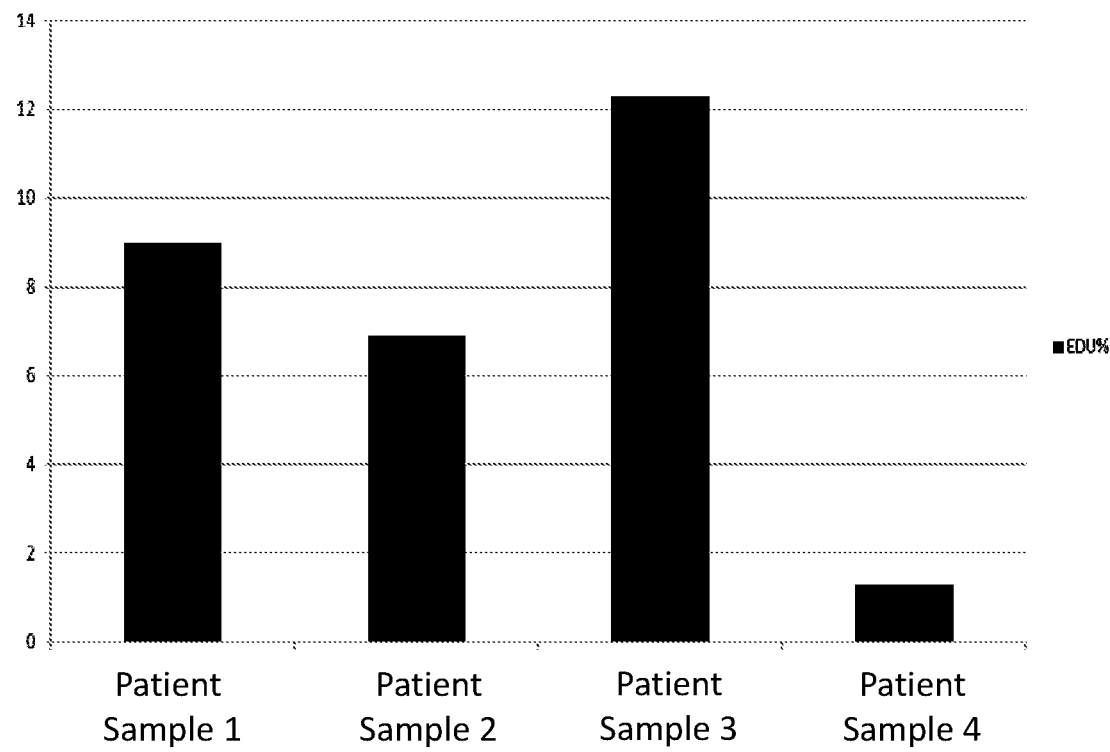
FIG. 2 shows that the tumor cells proliferated during a short-term suspension culture period, as measured by Edu incorporation (Sample 1 is from FIG. 1A, Sample 2 is from FIG. 1B, Sample 3 is from FIG. 1C, and Sample 4 is from FIG. 1D).

For direct patient samples, FIGS. 1A-1D show that tumor cells clusters were successfully isolated from colon/rectal tumors surgically remove from a patient, and cultured in suspension in a defined growth media. FIG. 2 shows that the tumor cells proliferated during a short-term suspension culture period, as measured by Edu incorporation (Sample 1 is from FIG. 1A, Sample 2 is from FIG. 1B, Sample 3 is from FIG. 1C, and Sample 4 is from FIG. 1D).

Figure 3A:
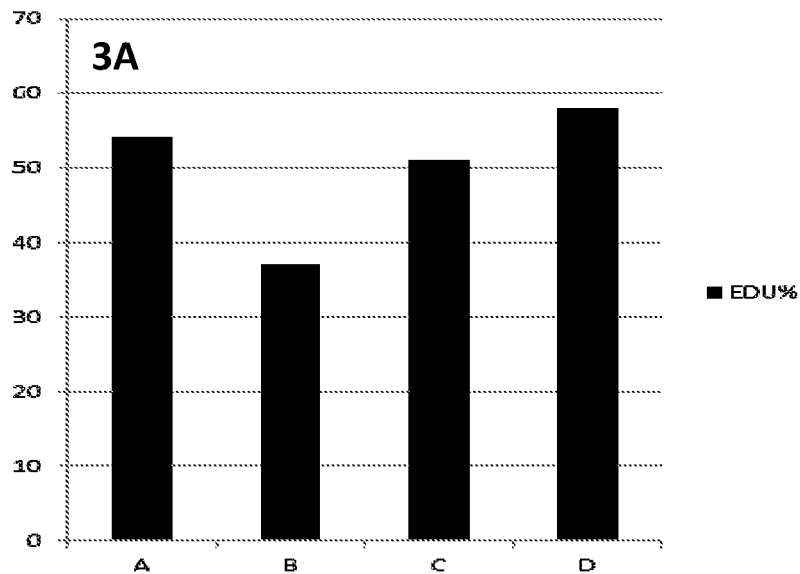
FIGS. 3A-3B show that short-term suspension cultures (within about 7 days) demonstrate the highest cell proliferation markers for the tumor cell clusters.
Figure 3B:
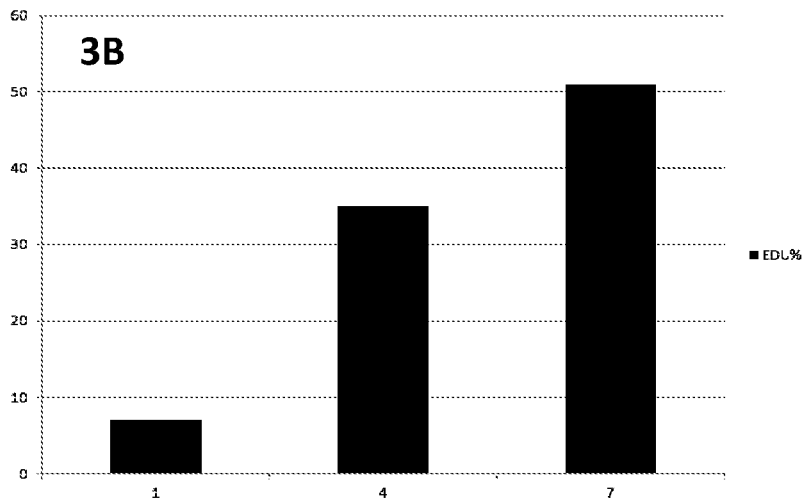

FIGS. 3A-3B show that short-term suspension cultures (within about 7 days) demonstrate the highest cell proliferation markers for the tumor cell clusters. FIG. 3A shows the proliferation markers for four different patient samples, and FIG. 3B shows the proliferation markers for one exemplary patient sample over the course of one week.

Figure 4:
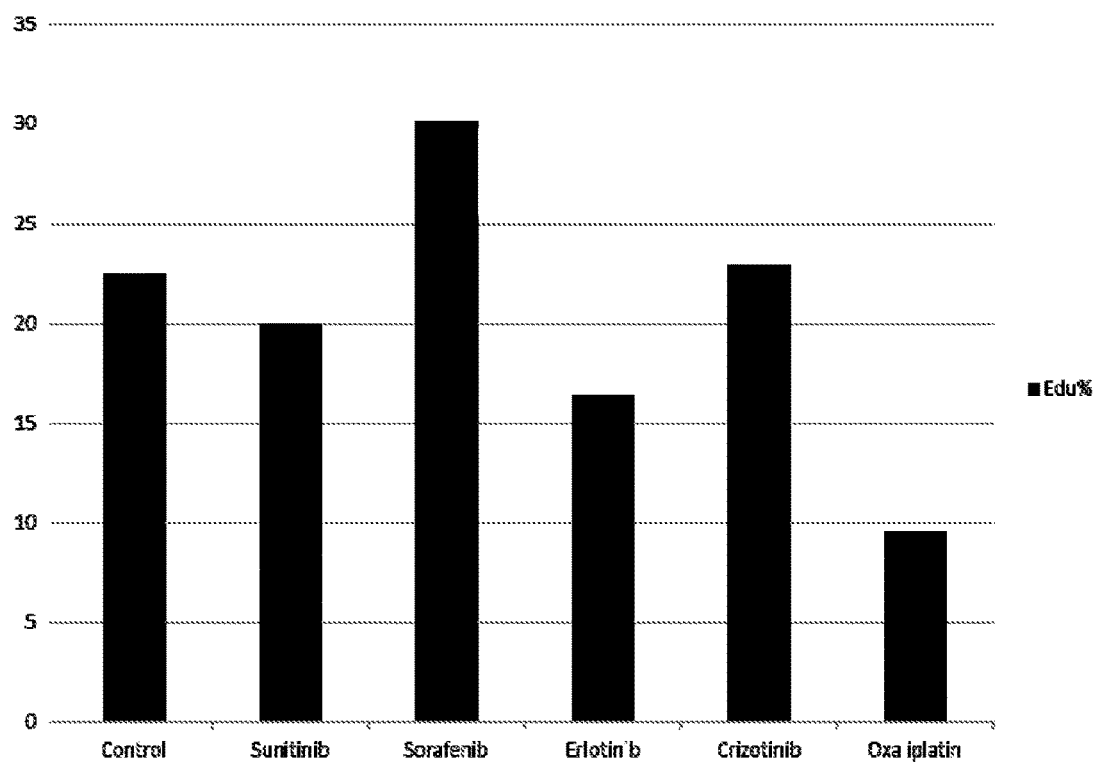
FIG. 4 shows that under test conditions (see FIG. 3B), the growth of tumor cell clusters is not completely inhibited by the tested drugs (sunitib, sorafenib, erlotinib, crizotinib, oxaliplatin), which is consistent with patient-derived xenografts (PDX) tumor responses to these drugs.

FIG. 4 shows that under these test conditions (see FIG. 3B), the growth of tumor cell clusters is not completely inhibited by the tested drugs (sunitib, sorafenib, erlotinib, crizotinib, oxaliplatin), which is consistent with patient-derived xenografts (PDX) tumor responses to these drugs. It was confirmed that the PDX-amplified tumors have similar morphology as those isolated from patient tumor tissues when cultured in suspension with defined media.

The invention claimed is:

1. A method of testing responsiveness of a human patient to a therapeutic agent, comprising obtaining or receiving primary colon cancer cells isolated directly from a tumor sample removed from the human patient partially enzyme digesting the primary colon cancer cells to obtain a population of tumor cell clusters from the human patient, wherein the tumor cell clusters have a diameter of from 40 to 100 1 M;

culturing the population of tumor cell clusters in a defined, serum-free medium suspension, wherein the medium suspension comprises nicotinamide, Wnt3A, noggin, R-spondin-1, and Y27632, wherein the medium suspension does not comprise an extracellular matrix component, and wherein the medium suspension provides at least 20-30% proliferation of the tumor cell clusters within 7 days;

administering the therapeutic agent to the medium suspension about 1, 2, 3, 4, 5, 6, or 7 days after day one or on the same day of culturing the population of tumor cell clusters in the medium suspension; and measuring tumor cell clusters proliferation and/or tumor cell apoptosis in the population of tumor cells clusters within about 7, 6, or 5 days of administering the therapeutic agent, wherein a decrease in tumor cell clusters proliferation and/or induction in tumor cell clusters apoptosis is indicative of responsiveness of the human patient to the therapeutic agent, and wherein a lack of decrease in tumor cell clusters proliferation and/or an induction in tumor cell clusters apoptosis is indicative of resistance of the human patient to the therapeutic agent.

2. The method of claim 1, comprising administering the therapeutic agent on the same day as culturing the population of tumor cell clusters in the medium suspension.

3. The method of claim 1, comprising administering the therapeutic agent at least one day after culturing the population of tumor cell clusters in the medium suspension.

4. The method of claim 1, wherein the step of measuring tumor cell clusters proliferation comprises measuring a cellular proliferation marker.

5. The method of claim 4, wherein the cellular proliferation marker is selected from one or more of $^{3}$H-thymidine, bromodeoxyuridine (BrdU), 5-ethynyl -2'-deoxyuridine (Edu), Ki-67, and proliferating cell nuclear antigen (PCNA).

6. The method of claim 1, wherein the step of measuring tumor cell apoptosis comprises measuring a cellular apoptosis marker.

7. The method of claim 6, wherein the cellular apoptosis marker is selected from one or more of fluorochrome-labeled inhibitors of Caspases (FLICA), caspase activation, poly ADP ribose polymerase (PARP) cleavage, DRAQ5, DRAQ7, and terminal deoxynucleotidyl transferase (TdT) dUTP nick-end labeling (TUNEL) assay.

8. The method of claim 1, wherein the medium suspension provides at least 60% proliferation of the human tumor cell clusters within 7 days.

\* \* \* \* \*